United States Patent
Rabhi et al.

(10) Patent No.: US 10,596,217 B2
(45) Date of Patent: *Mar. 24, 2020

(54) **COMPOSITIONS CONTAINING A *WITHANIA SOMNIFERA* EXTRACT INCUBATED WITH A FILAMENTOUS FUNGUS OF THE *BEAUVARIA* GENUS**

(71) Applicants: Ethnodyne, Paris (FR); Centre National de la Recherche Scientifique (CNRS), Paris (FR)

(72) Inventors: Chérif Rabhi, Bretigny sur Orge (FR); Léon Cariel, Paris (FR); Jamal Ouazzani, Massy (FR); Guillaume Arcile, Les Ulis (FR)

(73) Assignees: Ethnodyne, Paris (FR); Centre National de la Recherche Scientifique (CNRS), Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/566,188

(22) PCT Filed: Apr. 13, 2015

(86) PCT No.: PCT/IB2015/000796
§ 371 (c)(1),
(2) Date: Oct. 12, 2017

(87) PCT Pub. No.: WO2016/166565
PCT Pub. Date: Oct. 20, 2016

(65) Prior Publication Data
US 2018/0110820 A1 Apr. 26, 2018

(51) Int. Cl.
| | |
|---|---|
| *A61K 36/80* | (2006.01) |
| *A61K 36/81* | (2006.01) |
| *A61K 36/47* | (2006.01) |
| *A61P 25/28* | (2006.01) |
| *A61P 25/16* | (2006.01) |
| *A61K 36/68* | (2006.01) |

(52) U.S. Cl.
CPC ............ *A61K 36/81* (2013.01); *A61K 36/47* (2013.01); *A61K 36/68* (2013.01); *A61K 36/80* (2013.01); *A61P 25/16* (2018.01); *A61P 25/28* (2018.01); *A61K 2236/19* (2013.01); *A61K 2300/00* (2013.01)

(58) Field of Classification Search
None
See application file for complete search history.

(56) References Cited

U.S. PATENT DOCUMENTS

| | | | | |
|---|---|---|---|---|
| 2015/0224158 A1* | 8/2015 | Houle | ............ | A61K 36/53 424/733 |
| 2015/0305249 A1* | 10/2015 | Miller | ............ | A01G 18/00 47/1.1 |
| 2016/0101142 A1* | 4/2016 | Rabhi | ............ | A61K 36/81 424/725 |
| 2018/0042979 A1* | 2/2018 | Rabhi | ............ | A61K 36/80 |
| 2018/0289761 A1* | 10/2018 | Rabhi | ............ | A61K 36/81 |

FOREIGN PATENT DOCUMENTS

| | | |
|---|---|---|
| JP | 2013-001666 A | 1/2013 |
| WO | 2010/013254 A2 | 2/2010 |
| WO | 2011/114350 A2 | 9/2011 |
| WO | 2014/025905 A1 | 2/2014 |
| WO | 2014/202469 A1 | 12/2014 |

OTHER PUBLICATIONS

International Search Report dated Oct. 21, 2015, issued in corresponding International Application No. PCT/IB2015/000796, filed Apr. 13, 2015, 3 pages.
Kulkarni, S.K., and A. Dhir, "Withania somnifera: An Indian Ginseng," Progress in Neuro-Psychopharmacology & Biological Psychiatry 32(5):1093-1105, Jul. 2008.
Government of India, Biological Diversity Act, 2002, India.†

* cited by examiner
† cited by third party

*Primary Examiner* — Ralph J Gitomer
(74) *Attorney, Agent, or Firm* — Christensen O'Connor Johnson Kindness PLLC (57) ABSTRACT

The invention relates to a composition containing a *Withania somnifera* extract, obtained by fermentation by incubating the *Withania somnifera* extract with a filamentous fungus of the *Beauveria* genus. The composition can be used to treat or prevent α-synucleinopathies in a subject.

13 Claims, 9 Drawing Sheets

COMPOSITIONS CONTAINING A *WITHANIA SOMNIFERA* EXTRACT INCUBATED WITH A FILAMENTOUS FUNGUS OF THE *BEAUVARIA* GENUS

The invention relates to the use of a composition from a plant extract of *Withania somnifera*, to prevent, treat of delay the progression of α-synucleinopathies, including Parkinson disease.

The term α-synucleinopathies is usually employed to define a group of neurodegenerative disorders that show common pathologic proteinaceous accumulation of α-synuclein aggregates. In these diseases, α synuclein aggregates are deposited in selective vulnerable populations of neuronal and glial cells (Goedert M (1999) Philos Trans R Soc Lond B Biol Sci 354:1101-1118; Spillantini M. G & Goedert M (2000) Ann N Y Acad Sci 920:16-27; Trojanowski J. Q & Lee V. M (2003) Ann N Y Acad Sci 991:107-110.).

The aggregation mechanism of alpha-synuclein is uncertain. There is evidence of a structured intermediate rich in beta structure that can be the precursor of aggregation and, ultimately, Lewy bodies.

From a clinical point of view, α-synucleinopathies include symptomatically heterogeneous disorders, among them Lewy bodies-associated diseased such as PD, dementia with Lewy bodies, also known as Lewy body dementia, diffuse Lewy body disease, cortical Lewy body disease, and senile dementia of Lewy type, multiple system atrophy, Lewy bodies dysphagia as well as neurodegeneration with brain iron accumulation type I and pure autonomic failure. Lewy body disease is one of the most common causes of dementia in the elderly. Dementia is the loss of mental functions severe enough to affect normal activities and relationships.

Alpha-synuclein is protein of unknown function primarily found in neural tissue, making up as much as 1% of all proteins in the cytosol of brain cells. It is predominantly expressed in the neocortex, hippocampus, substantia nigra, thalamus, and cerebellum. It is predominantly a neuronal protein, but can also be found in the neuroglial cells. Smaller amounts are found in the heart, muscles, and other tissues. In the brain, alpha-synuclein is found mainly at the tips of nerve cells (neurons) in specialized structures called presynaptic terminals. Within these structures, alpha-synuclein interacts with phospholipids and proteins. Presynaptic terminals release chemical messengers, called neurotransmitters, from compartments known as synaptic vesicles. The release of neurotransmitters relays signals between neurons and is critical for normal brain function.

Although the function of alpha-synuclein is not well understood, studies suggest that it plays an important role in maintaining a supply of synaptic vesicles in presynaptic terminals. It may also help regulate the release of dopamine, a type of neurotransmitter that is critical for controlling the start and stop of voluntary and involuntary movements.

Alpha-synuclein is specifically upregulated in a discrete population of presynaptic terminals of the brain during a period of acquisition-related synaptic rearrangement. It has been shown that alpha-synuclein significantly interacts with tubulin, and that alpha-synuclein may have activity as a potential microtubule-associated protein.

Apparently, alpha-synuclein is essential for normal development of the cognitive functions. Knock-out mice with the targeted inactivation of the expression of alpha-synuclein show impaired spatial learning and working memory.

Parkinson's disease (PD) is the second most common neurodegenerative disorder in the United States.

The predominant motor symptoms of PD including slow movement, resting tremor, rigidity and gait disturbance are caused by the loss of dopaminergic neurons in the substantia nigra (SN). Although the etiology of PD remains so far unknown, both genetic and environmental factors appear to play a role (Vila, M. & Przedborski, S. (2004). Nat. Med., 10 Suppl, S58-S62).

Cognitive dysfunction in Parkinsons's disease (PD) is a prominent non-motor symptom in PD, highly contributing to morbidity and mortality in this disease. The etiologies of cognitive impairments in PD patients are heterogenous and include executive dysfunctions, thought disorders, and very often manifest in dementia, which affects up to 80% of patients. Accordingly, even the structural changes leading to dementia in Parkinsons's disease are not equivalent and clearly differ from the structural brain changes in Alzheimer's disease.

Several studies have shown an association between the number of cortical Lewy bodies and dementia (Hurtig H. I et al., 2000, Neurology 54(10):1916-1921; Aarsland, D. et al., 2005, Mov Disord 20:1255-1263).

Among the strategies for treating synucleinopathies are compounds that inhibit aggregation of alpha-synuclein. It has been shown that the small molecule cuminaldehyde inhibits fibrillation of alpha-synuclein.

Current pharmaceutical treatments for Parkinson's disease focus on dopaminergic agents, which either mimic dopamine, or increase levels of dopamine in the body. The most common therapy is levodopa, which is a metabolic precursor of dopamine. However, long term levodopa therapy is often accompanied by dyskinesias, which are sudden, involuntary movements.

It has been reported that extracts of *Withania somnifera*, *Emblica officinalis* and *Bacopa monnieri* show anti-angiogenic activity. However, the extracts of these plants were not used because of the high toxicity related to the obtaining of the extracts and, in particular, the extract from *Withania somnifera*.

Surprisingly, the applicant has found that, by affecting the toxicity of the extracts of the plant *Withania somnifera*, by combining an extraction step and a fermentation step using filamentous fungi, it is possible to use the detoxified extract to treat PD, dementia with Lewy bodies, also known as Lewy body dementia, diffuse Lewy body disease, cortical Lewy body disease, and senile dementia of Lewy type, multiple system atrophy, Lewy bodies dysphagia as well as neurodegeneration with brain iron accumulation type I and pure autonomic failure.

The purpose of the invention is therefore to use a non-toxic composition based on extracts of *Withania somnifera*, to prevent, treat or delay the progression of α-synucleinopathies.

Other objects, features, aspects and advantages of the invention will appear more clearly on reading the description and examples that follow:

The invention is directed to the use of a composition containing a *Withania somnifera* extract for its use to prevent, treat or delay the progression of α-synucleinopathies a mammal. Preferably, the mammal is a human.

Preferably, the *Withania somnifera* extract has been fermented by its incubation with a filamentous fungus in a suitable environment.

The *Withania somnifera* plant is obtained from India. The root of this plant is marketed by Alp Erbo (Marseille).

The process of production of extracts according to the invention can be found in WO 2014/202469. Briefly, the plants are fermented in presence of a filamentous fungus of the family Cordycipitaceae, preferably the genus *Beauveria*. More preferably, the filamentous fungus is derived from the strain *Beauveria bassiana*, more particularly the strain having reference ATCC 7159.

The controlled fermentation detoxifies the *Withania Somnifera* extract by a series of biocatalysis of various molecules contained in this extract and, more particularly, the chemical family of withanolide aglycones, the substances mainly responsible for the toxicity of the extract.

The term "detoxification" is used to mean elimination by the microorganism of potentially toxic molecules in the medium.

Preferably, after the fermentation, filtration, the medium is then subjected to sterilisation steps, preferably by ultra-filtration, in order to obtain the solution which constitutes the plant extract.

The plant extract of the invention contain *Withania somnifera* but may also contain at least one of the following extracts *Emblica officinalis*, originating in India and marketed by Infrag, Bengalore), *Bacopa monnieri* (India) marketed by Alp Erbo (Marseille), *Punica granatum* (China) (Shanghai Brightol International Co, Ltd (Shanghai), *Curcuma longa* (India) (Omnipharm, Chambery), *Piper longum* (Thailand) (Omnipharm, Chambery), or *Calendula officinalis* (China) (Shanghai Brightol International Co, Ltd (Shanghai), using the same procedure), by independent extraction steps for each plant extract used in the realisation of the said preparation.

Advantageously, the composition used in this invention includes, by weight, between 5 and 100 g/L of *Withania somnifera*, preferably 20 g/L. Preferentially, this composition also includes one of the following extracts, expressed by weight:

between 5 and 100 g/L of *Emblica officinalis*, preferably 15 g/L,
between 5 and 100 g/L of *Bacopa monnieri*, preferably 15 g/L,
between 5 and 50 g/L of *Punica granatum*, preferably 10 g/L,
between 5 and 250 g/L of *Curcuma longa*, preferably 20 g/L,
between 20 and 50 mg/L of *Piper longum*, preferably 30 mg/L,
between 5 and 50 g/L of *Calendula officinalis*, preferably 10 g/L, Preferably, the composition used in this invention comprises an extract of the plants *Withania somnifera, Emblica officinalis* and *Bacopa monnieri*. More preferably, the composition according to the invention comprises a quantity by weight of *Withania somnifera* at a concentration of 20 g/L, of *Emblica officinalis* at a concentration of 15 g/L and of *Bacopa monnieri* at a concentration of 15 g/L.

The compositions according to the invention are used to treat or prevent Parkinson disease, dementia lewis bodies, multiple system atrophy, Lewis bodies dysphagia, neuroaxonal dystrophies and neurodegeneration with brain iron accumulation type I.

Motor impairments, or impairments of motor function, that can be treated in accordance with the methods described herein include, without limitation: general mobility impairments, walking impairments, gait impairments (e.g., gait freezing), unwanted acceleration of walking, postural instability, stooped posture, increase in falls, dystonia, dyskinesia, tremor, rigidity, bradykinesia, micrographia, dexterity impairment, motor coordination impairment, decreased arm swing, akathisia, speech impairment, problematic swallowing, sexual dysfunction, cramping and drooling. In some embodiments, the motor impairment treated in accordance with the methods described herein is either dyskinesia, dystonia, or motor fluctuation. In other embodiments, the motor impairment is either a tremor, bradykinesia, or rigidity. In certain embodiments, the motor impairment treated in accordance with the methods described herein is an impairment in general mobility. In some embodiments, the motor impairment or the general mobility impairment treated in accordance with the methods described herein is an impairment in walking. In one embodiment, the walking impairment treated in accordance with the methods described herein is a decrease in walking speed. In yet another embodiment, the walking impairment treated in accordance with the methods described herein is unwanted acceleration in walking. In some embodiments, the motor impairment treated in accordance with the methods described herein is increase in falls. In certain embodiments, the motor impairment treated in accordance with the methods described herein is a balance impairment, such as postural instability or postural imbalance.

In some embodiments, there is a method of treating α-synucleinopathies in an individual, comprising the step of delivering to the individual a therapeutic amount of a plant extract composition, such that said α-synucleinopathy in a subject is treated or prevented, wherein said composition contains a plant extract of *Withania somnifera*.

The α-synucleinopathies comprise Parkinson disease, dementia lewis bodies, multiple system atrophy, Lewis bodies dysphagia, neuroaxonal dystrophies and neurodegeneration with brain iron accumulation type I.

The invention provides for a method of treatment of patients who have Parkinson's disease (PD). In particular, the invention provides for treatment of one or more impairments associated with PD in a patient with PD.

In some embodiments, the method prevents, treats or delays the progression of dementia associated with PD in a subject in need of such treatment, comprising administering to said subject a therapeutic effective amount of a composition of the invention.

The composition according to the invention is formulated for oral or parenteral administration.

A person skilled in the art of pharmaceutical formulation will implement the various useful forms for administration of the compositions and/or supplements of the invention. The compositions may be in liquid, gel, emulsion, solid or injectable form.

The composition used may additionally include suspensions, emulsions, syrups containing conventionally used inert diluents, and possibly other substances such as wetting agents, sweeteners, preservatives, thickeners, colourings or any other substance known to a person skilled in the art suitable for oral administration, in particular ((sodium sorbate (E201) (Sigma-Aldrich), anthocyanin (E163) (FBC Industries, USA), sodium metabisulphite (E223) (Sigma-Aldrich), alpha-tocopherol (E307) (FBC Industries, USA).

The composition used may also comprise solvents or other excipients such as water, propylene glycol, vegetable oils or other suitable organic solvents.

The term "excipient" is used to mean any compound which does not interfere with the effectiveness of the biological activity of the composition according to the invention, and which is not toxic to the host to which it is administered.

The composition used may also contain adjuvants, such as wetting agents, isotoning agents, emulsifiers, salts or any other substances known to a person skilled in the art that can be used as adjuvants (Polydimethylsiloxane, polyvinyl alcohol (PVA), hydrogels (Carbopol), polyvinylpyrrolidone, hydroxypropyl cellulose (HPC), poloxamer 188, EDTA, chlorobutanol) (Lubrizol, France, Dow Corning, USA).

Advantageously, the composition may comprise other substances such as vitamins, mineral salts, a pharmaceutically acceptable vector, stabilisers, antioxidants, or any other substance known to a person skilled in the art and intended to be integrated into a drug.

Preferably, the composition is liquid, orally administrable and contains at least a non-toxic extract of *Whitania somnifera*, some preservatives, vitamins, water and salt.

More preferably, the preservatives are potassium sorbate or benzoate. The vitamin may be riboflavin (vitamin B2).

The therapeutic composition used in the method of the invention is administered in a pharmaceutically acceptable vehicle.

The terms "pharmaceutically acceptable vehicle" is used to mean any vehicle which does not interfere with the effectiveness of the biological activity of the composition according to the invention and which is not toxic to the host to which it is administered.

The composition obtained is usable as a medicinal product for a mammal, and more particularly for humans, to assist in the treatment or prevention of disorders or diseases linked to α-synucleinopathies and in particular PD.

The term "medicinal product" is used to mean a product containing an accurate dose of said preparation according to European directive 65/65/EC, namely any substance or composition described as possessing curative or preventive properties with respect of human or animal disease. For example, the medicinal product containing said preparation at therapeutic doses can be administered orally as a capsule or a tablet, or injected via any other route to confer the beneficial effects.

An appropriate dosage of the therapeutic composition can be determined by one of skill in the art, taking into consideration the findings described herein together with typical factors such as the body mass of the patient, the physical condition of the patient, and so on. The dosage should contain the therapeutic composition in an amount that is effective for treating α-synucleinopathies, including PD.

The drug can be administered daily, weekly, or on an intermittent basis. For example, the drug can be administered for three months on, followed by one month off, or for one month on, followed by one week off, or under other dosing schedules as can be determined by one skilled in the field.

The particular dose selected will depend upon the mode of administration and dosing regimen selected. One preferred schedule is a once daily oral dosing schedule. When longer periods of time are prescribed between each application (typically the case for i.v administration), each unit dose may be larger than when daily dosages are provided.

The daily dose of the compositions used may vary according to the needs and severity of symptoms of the patient and according to the route. Typically, the daily dose is between 10 mg/mL and 300 mg/mL of the solution after fermentation.

Preferably, the daily dose for an adult human is between 30 and 100 mg/mL of the solution after fermentation.

The present invention will be explained in further detail by way of non-limiting examples below, which make reference to the appended drawings. The following methods were used in the experiments described in the examples that follow the description of the methods.

Example 1: Composition WEB-1 Before Fermentation

The composition WEB-1 contains a commercial extract of *Withania Somnifera* at a concentration of 20 g/L, of *Emblica officinalis* at a concentration of 15 g/L, of *Bacopa monnieri* at a concentration of 15 g/L.

A solution of 100 mL is made in water. After lyophilization, 3.8 g of a beige powder is obtained.

Example 2: Strain of Filamentous Fungus *Beauveria bassiana*

The strain *Beauvaria Bassiana* (reference ATCC 7159) has been cultivated in a medium containing 0.5 g/L $KH_2PO_4$; 1 g/L $KH_2PO_4$; 1 g/L $MgSO_4$; 2 g/L $NaNO_3$; 0.5 g/L KCl; 0.02 g/L $FeSO_4$; 30 g/L glucose (all reagents from Sigma-Aldrich, France) and 10 g/L of corn steep liquor (Roquette, France).

The culture was then agitated at 200 rotations per minute, for 72 hours at 27° C. It was then filtered by non-sterile methods on a filter paper to separate the fungal biomass from the culture medium. The fungal biomass was then washed thoroughly with water.

Example 3: Composition WEB-2 Used in the Invention

The composition WEB-1 as in example 1 is added to the fresh fungal biomass of example 2 using 60 g of biomass per liter of composition WEB-1 containing 50 g of glucose.

After incubation, this seeded composition was agitated at 200 rpm for 5 days at a temperature of 27° C.

After 5 days, the incubation medium was filtered on a filter paper, the samples for HPLC assay were also filtered using a 0.45 micron filter (Ait-France, ref: SFNY 013045N).

The brownish solution obtained which was then lyophilized during 5 days to produce dried beige powder.

Example 4: Composition WE-2 Used in the Invention

The composition WE-1 contains an commercial extract of *Withania Somnifera* at a concentration of 20 g/L, and of *Emblica officinalis* at a concentration of 15 g/L.

To 100 mL of such a solution, are added 5 g of glucose and 6 g of biomass of example 2.

After having treated and lyophilized the solution like in example 3, 4.13 g of a beige powder is obtained.

The markers identified in the composition WE-2 were Withanoside IV, Withanoside VI and gallic acid.

Example 5: Composition WB-2 Used in the Invention

The composition WB-1 contains an extract of *Withania Somnifera* at a concentration of 20 g/L, and of *Bacopa Monnieri* at a concentration of 15 g/L.

To 100 mL of such a solution, are added 5 g of glucose and 6 g of biomass of example 2.

After having treated and lyophilized the solution like in example 3, 2.62 g of a beige powder is obtained.

The markers identified in the composition WB-2 were Withanoside IV, Withanoside VI, Bacoside A3, Bacopaside X and Bacopasaponin C.

Example 6: Composition BE-2 Used in the Invention

The composition BE-2 contains an extract of *Bacopa Monnieri* at a concentration of 15 g/L, and of *Emblica officinalis* at a concentration of 15 g/L.

To 100 mL of such a solution, are added 5 g of glucose and 6 g of biomass of example 2.

After having treated and lyophilized the solution like in example 3, 2.62 g of a beige powder is obtained.

The markers identified in the composition BE-2 were Bacopaside X, Bacopasaponin C and gallic acid.

Example 7: Composition WEB-4 According to the Invention

The composition WBE-4 contains an extract of *Withania Somnifera* at a concentration of 40 g/L, of *Bacopa Monnieri* at a concentration of 15 g/L, and of *Emblica officinalis* at a concentration of 15 g/L.

To 100 mL of such a solution, are added 5 g of glucose and 6 g of biomass of example 2.

After having treated and lyophilized the solution like in example 3, 4.23 g of a beige powder is obtained.

Example 8: Composition WEB-6 Used in the Invention

The composition WEB-6 contains an extract of *Withania Somnifera* at a concentration of 20 g/L, of *Bacopa Monnieri* at a concentration of 15 g/L, and of *Emblica officinalis* at a concentration of 30 g/L.

To 100 mL of such a solution, are added 5 g of glucose and 6 g of biomass of example 2.

After having treated and lyophilized the solution like in example 3, 4.22 g of a beige powder is obtained.

Example 9: Composition WEB-8 Used in the Invention

The composition WEB-8 contains an extract of *Withania Somnifera* at a concentration of 20 g/L, of *Bacopa Monnieri* at a concentration of 30 g/L, and of *Emblica officinalis* at a concentration of 15 g/L.

To 100 mL of such a solution, are added 5 g of glucose and 6 g of biomass of example 2.

After having treated and lyophilized the solution like in example 3, 3.76 g of a beige powder is obtained.

Example 10: Neuroprotective Effect Following Exposure to 6OHDA

This study investigated the neuroprotective effect of the plant extract of the invention on rat primary mesencephalic cultures following exposure to 6OHDA.

Epidemiological studies suggest that the use of pesticides increases the risk of PD, possibly via reduced activity of complex I in the mitochondrial respiratory chain in the substantia nigra and result in the pathogenesis of PD.

6-hydroxydopamine (6-OHDA), a H2O2 pro-oxidant a natural dopaminergic catabolite that accumulates in Parkinson's disease-affected brains appears to strongly contribute to this pathology (Giordano S, et al., PLoS One. 2012; 7(9)).

a) Culture of Mesencephalic Neurons

Rat dopaminergic neurons were cultured as described by Schinelli et al., 1988 (Visanji et al., 2008 FASEB J. 2008; 22(7):2488-97. Briefly, the midbrains obtained from 15-day old rat embryos (Janvier Labs, France) were dissected under a microscope. The embryonic midbrains were removed and placed in ice-cold medium of Leibovitz (L15, Batch 4290114, Pan Biotech, Germany) containing 2% of Penicillin-Streptomycin (PS, Batch 1451013, Pan Biotech) and 1% of bovine serum albumin (BSA, Batch K030913, Pan Biotech). The ventral portion of the mesencephalic flexure, a region of the developing brain rich in dopaminergic neurons, was used for the cell preparations.

The midbrains were dissociated by trypsinisation for 20 min at 37° C. (Trypsin 0.05%, EDTA 0.02% (Batch 7310713, PanBiotech). The reaction was stopped by the addition of Dulbecco's modified Eagle's medium (DMEM, Batch 9710913, PanBiotech) containing DNAase I grade II (0.1 mg/mL, Batch H131108, PanBiotech) and 10% of foetal calf serum (FCS, Batch 41Q7218K, Gibco). Cells were then mechanically dissociated by 3 passages through a 10 mL pipette. Cells were then centrifuged at 180×g for 10 min at +4° C. on a layer of BSA (3.5%) in L15 medium. The supernatant was discarded and the cell pellets were re-suspended in a defined culture medium consisting of Neurobasal (Batch 1576979, Invitrogen, France) supplemented with 2% of B27 (Batch 1589889, Invitrogen), 2 mM of L-glutamine (Batch 8150713, PanBiotech), 2% of PS solution, 10 ng/mL of Brain-derived neurotrophic factor (Batch H140108, PanBiotech) and 1 ng/mL of Glial-Derived Neurotrophic Factor (Batch H130917, Pan Biotech) Viable cells were counted in a Neubauer cytometer using the trypan blue exclusion test. The cells were seeded in supplemented neurobasal medium at a density of 40 000 cells/well in 96 well-plates pre-coated with poly-L-lysine (Batch 3102256, Corning Biocoat) and maintained in a humidified incubator at 37° C. in 5% CO2/95% air atmosphere. Half of the medium was changed every 2 days with fresh medium.

On day 6 of culture, the medium was removed and fresh medium was added, without or with 6-OHDA (Sigma, Batch: 083M4624V) at 20 µM diluted in control medium, 6 wells per condition were assessed.

b) 6-OHDA Exposure

On day 6 of culture, the WEB-2 plant extract of example 1 (50, 5 mg/mL, 500, 50, 5 µg/mL and 500 ng/mL) was diluted in culture medium and then pre-incubated with mesencephalic neurons for 1 hour before the 6-OHDA application or 4, 8 or 12 h after 6-OHDA application. 6OHDA solution was added to a final concentration of 20 µM diluted in control medium.

c) Immunostaining

After 24 hours, cells were fixed by a solution of 4% paraformaldehyde (Batch SLBF7274V, Sigma) in PBS (Batch 7560414, PanBiotech), pH=7.3 for 20 min at room temperature. The cells were washed again twice in PBS, permeabilized and non-specific sites were blocked with a solution of PBS containing 0.1% of saponin (Batch BCBJ8417V, Sigma, France) and 1% FCS for 15 min at room temperature. Then, cells were incubated with Monoclonal Anti-Tyrosine Hydroxylase antibody produced in mouse (Batch 101M4796, Sigma) at dilution of 1/10000 in PBS containing 1% FCS, 0.1% saponin, for 2 h at room temperature. This antibody was revealed with Alexa Fluor 488 goat anti-mouse IgG (Batch 1397999, Molecular probe, France) at the dilution 1/800 in PBS containing 1% FCS, 0.1% saponin, for 1 h at room temperature.

Tyrosine hydroxylase (TH) is involved in the conversion of phenylalanine to dopamine. As the rate-limiting enzyme in the synthesis of catecholamines, tyrosine hydroxylase has a key role in the physiology of adrenergic neurons and is regularly used as a marker for dopaminergic neurons.

d. Results

The immunolabeled cultures were automatically examined with ImageXpress (Molecular Devices, United Kingdom) equipped with a LED at ×10 magnification. For each condition (6 culture wells), 20 automatically fields per well (representing ~80% of the total surface of the well) were analyzed. The total number of TH neurons was automatically analyzed using MetaXpress software (Molecular Devices).

Data were expressed in percentage of control conditions (no MPP$^+$=100%) in order to express the MPP$^+$ injury. All values were expressed as mean+/−SEM (s.e.mean) of the 6 wells with statistical analyses on the different conditions (ANOVA followed by Dunnett's test when allowed, using GraphPad Prism software).

Figure 1:
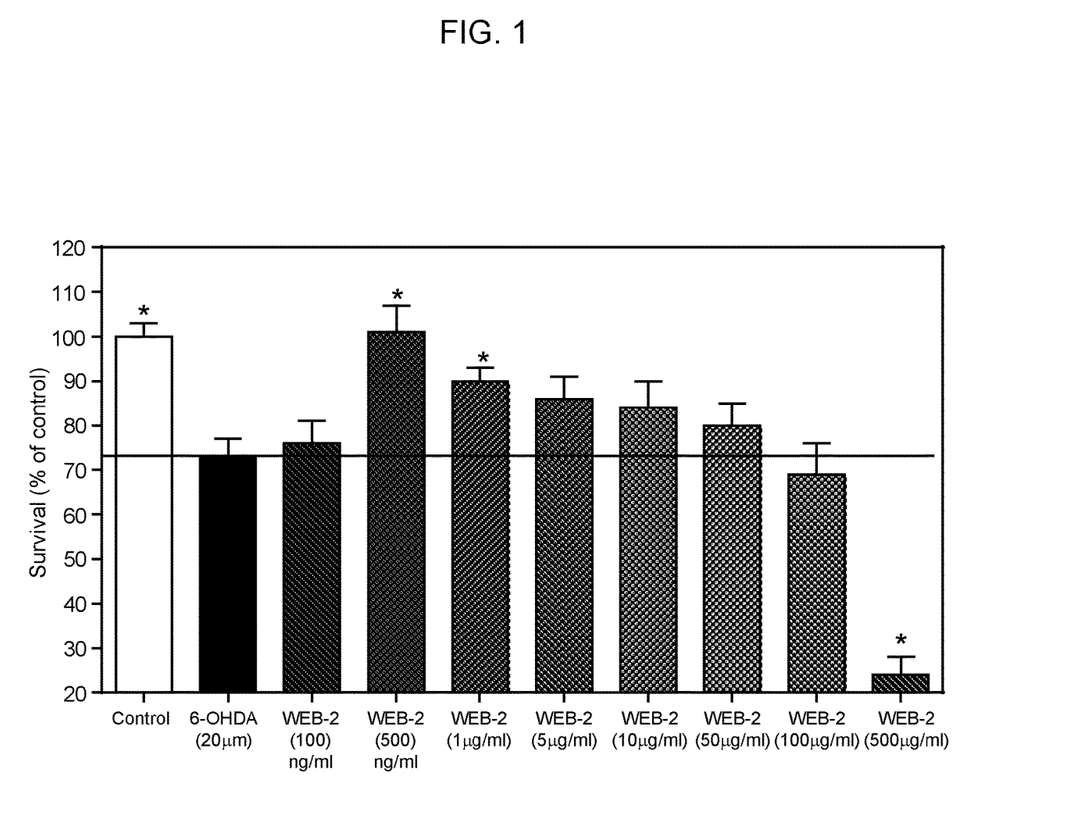
FIG. 1: Effect of 6-OHDA (20 μM, 24 hours) in presence or absence of WEB-2 at 1 hour before 6-OHDA (different concentrations) on TH positive dopaminergic neuron survival of primary mesencephalic culture. Data were expressed as percentage of control as mean±SEM (100%=no 6-OHDA). *p<0.05 vs 6-OHDA (one way ANOVA followed by PLSD Fisher's test).

6-OHDA (20 µM-24 h) induced a significant cell death (>25%). With WEB-2 pre-incubated 1 h before 6-OHDA application, a full significant protective effect was observed (100% of survival) for the dose of 500 ng/mL. The highest dose (1 µg/mL) significantly induced protective effect (by 86%). The effect progressively disappeared with the dose, at the highest concentration (500 µg/mL) WEB-2 became toxic. The lowest dose (100 ng/mL) did not show any effect on TH positive neurons (FIG. 1).

Figure 2:
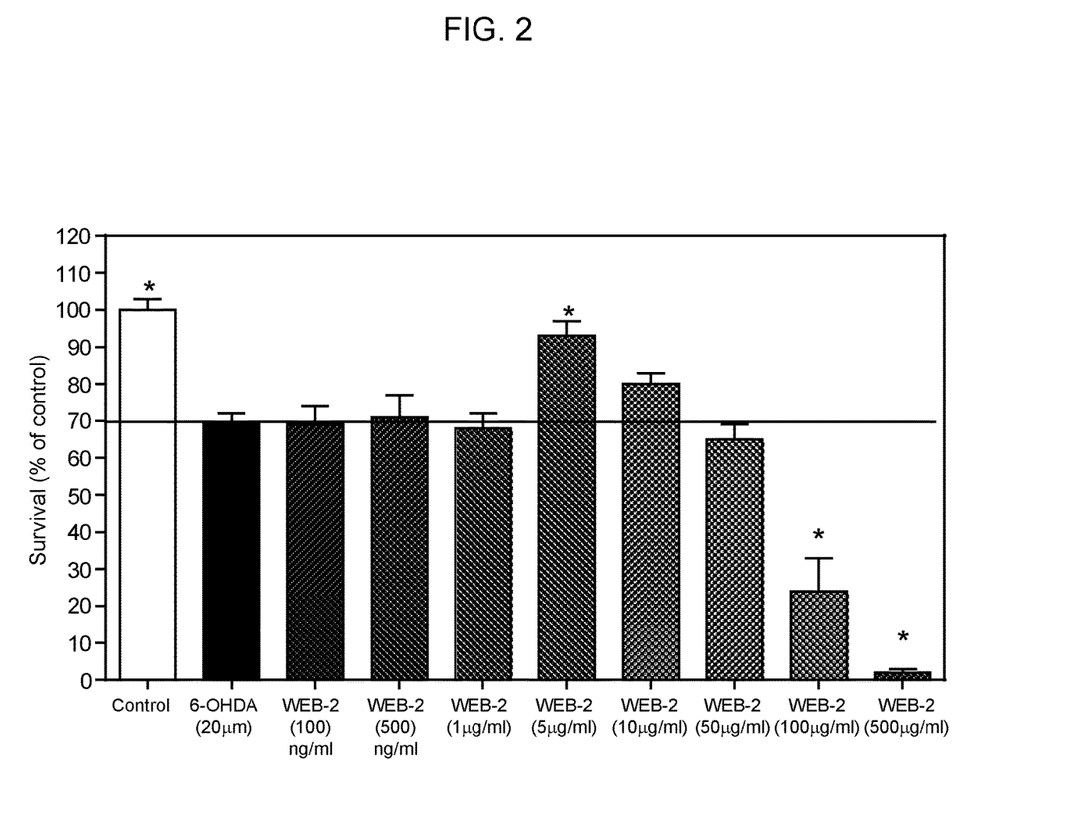
FIG. 2: Effect of 6-OHDA (20 μM, 24 hours) in presence or absence of WEB-2 at 4 hours after 6-OHDA (different concentrations) on TH positive dopaminergic neuron survival of primary mesencephalic culture. Data were expressed as percentage of control as mean±SEM (100%=no 6-OHDA). *p<0.05 vs 6-OHDA (one way ANOVA followed by PLSD Fisher's test).

WEB-2 added 4 h after the application of 6-OHDA, totally reversed the deleterious effect of 6-OHDA (5 µg/mL) significant protective effect was observed (~100% of survival). The doses 100 and 500 µg/mL of WEB-2 are toxic. The lowest concentrations (between 100 ng/mL up to 1 µg/mL) did not show any protective effect (FIG. 2).

Figure 3:
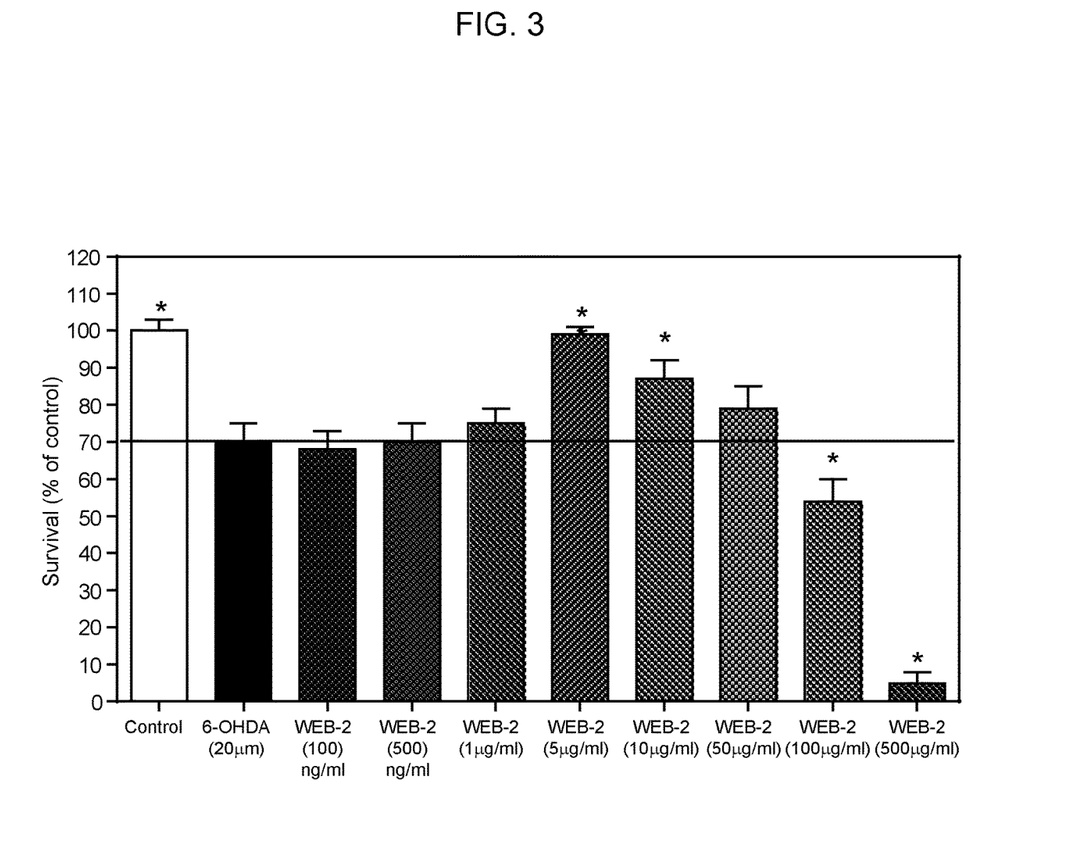
FIG. 3: Effect of 6-OHDA (20 µM, 24 hours) in presence or absence of WEB-2 at 8 hours after 6-OHDA (different concentrations) on TH positive dopaminergic neuron survival of primary mesencephalic culture. Data were expressed as percentage of control as mean±SEM (100%=no 6-OHDA). *p<0.05 vs 6-OHDA (one way ANOVA followed by PLSD Fisher's test).

WEB-2 added 8 h after the toxin application showed protective effect (~100% of survival for 5 µg/mL), 10 µg/mL was efficient. The 2 highest doses were toxic (FIG. 3).

Figure 4:
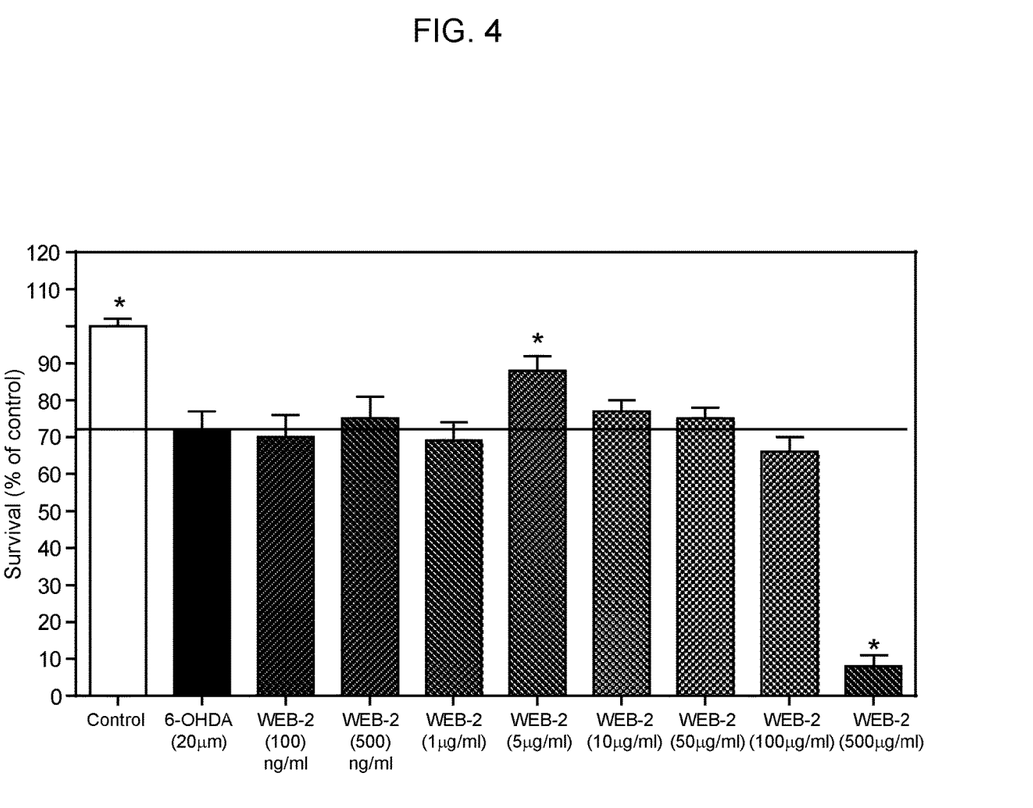
FIG. 4: Effect of 6-OHDA (20 µM, 24 hours) in presence or absence of WEB-2 at 12 hours after 6-OHDA (different concentrations) on TH positive dopaminergic neuron survival of primary mesencephalic culture. Data were expressed as percentage of control as mean±SEM (100%=no 6-OHDA). *p<0.05 vs 6-OHDA (one way ANOVA followed by PLSD Fisher's test).

Added 12 h after the 6-OHDA application, WEB-2 was still able to protect neurons from death (still at 5 µg/mL). In this procedure (12 h after 6-OHDA application) only the highest doses showed toxicity (500 µg/mL). All the other doses were inactive (FIG. 4).

e) Conclusion

6-OHDA (20 µM-24 h) applied on primary mesencephalic culture induced a significant TH positive neuron (dopaminergic neurons) death.

WEB-2 was active and protect dopaminergic neurons from the injury induced by 6-OHDA.

WEB-2 when added in pre-incubation protects neurons at the concentrations of 500 ng/mL and 1 µg/mL; and displayed toxicity at the highest doses (500 µg/mL)

By contrast, when added some hours after 6-OHDA, when the toxin has already started to display its toxic effect on the mitochondria, WEB-2 reversed damages at highest dose: 5 µg/mL.

The range of the most active doses of WEB-2 seemed starting at 500 µg/mL (when added in prevention) and at 5 µg/mL when added after damages occurred.

Example 11: Neuroprotective Effect Following Exposure to MPP+

This study investigated the neuroprotective effect of the plant extract of the invention on rat primary mesencephalic cultures following exposure to 1-methyl-4-phenyl pyridinium (MPP$^+$).

The neurotoxic 1-methyl-4-phenyl-1,2,3,6-tetrahydropyridine (MPTP) is a specific dopaminergic neuronal toxin. MPTP is converted to MPP$^+$ by astroglia and then causes specific dopaminergic neuronal death in the SN, thus leading to the clinical symptoms of PD in humans, primates and mice ((Visanji et al., 2008 FASEB J. 2008; 22(7):2488-97, Giordano S, et al., PLoS One. 2012; 7(9)). MPP$^+$ selectively enters dopamine neurons via the dopamine transporter and also blocks complex I of the mitochondrial respiratory chain.

In such assay, Brain Derived Growth Factor (BDNF) was used as standard molecule.

a) Culture of Mesencephalic Neurons

The mesencephalic neurons were cultivated as in preceding example.

On day 6 of culture, the medium was removed and fresh medium was added, without or with MPP$^+$ (Batch 092M4729V, Sigma, France) at 4 µM diluted in control medium. 6 wells per condition were assessed.

b) MPP+ Exposure

On day 6 of culture, the WEB-2 plant extract (500 ng/mL, 1, 5, 10, 50, 100, 500 µg/mL and 1 mg/mL) was solved in culture medium and then pre-incubated with primary mesencephalic neurons for 1 hour before the MPP$^+$ application. MPP$^+$ solution was added to a final concentration of 4 µM diluted in control medium in presence of WEB-2 and tested after 48 h on one primary culture in 96 well plates (6 wells per conditions).

a) Immunostaining

The cells were fixed, washed, permeabilized and non-specific sites were blocked. Then, cells were incubated with Monoclonal Anti-Tyrosine Hydroxylase and revealed with Alexa Fluor 488 goat anti-mouse IgG like in example 10.

b) Results

The immunolabeled cultures were automatically examined with ImageXpress (Molecular Devices, United Kingdom) equipped with a LED at ×10 magnification. For each condition (6 culture wells), 20 automatically fields per well (representing ~80% of the total surface of the well) were analyzed. The total number of TH neurons was automatically analyzed using MetaXpress software (Molecular Devices).

Data were expressed in percentage of control conditions (no MPP$^+$=100%) in order to express the MPP$^+$ injury. All values were expressed as mean+/−SEM (s.e.mean) of the 6 wells with statistical analyses on the different conditions (ANOVA followed by Dunnett's test when allowed, using GraphPad Prism software).

Figure 5:
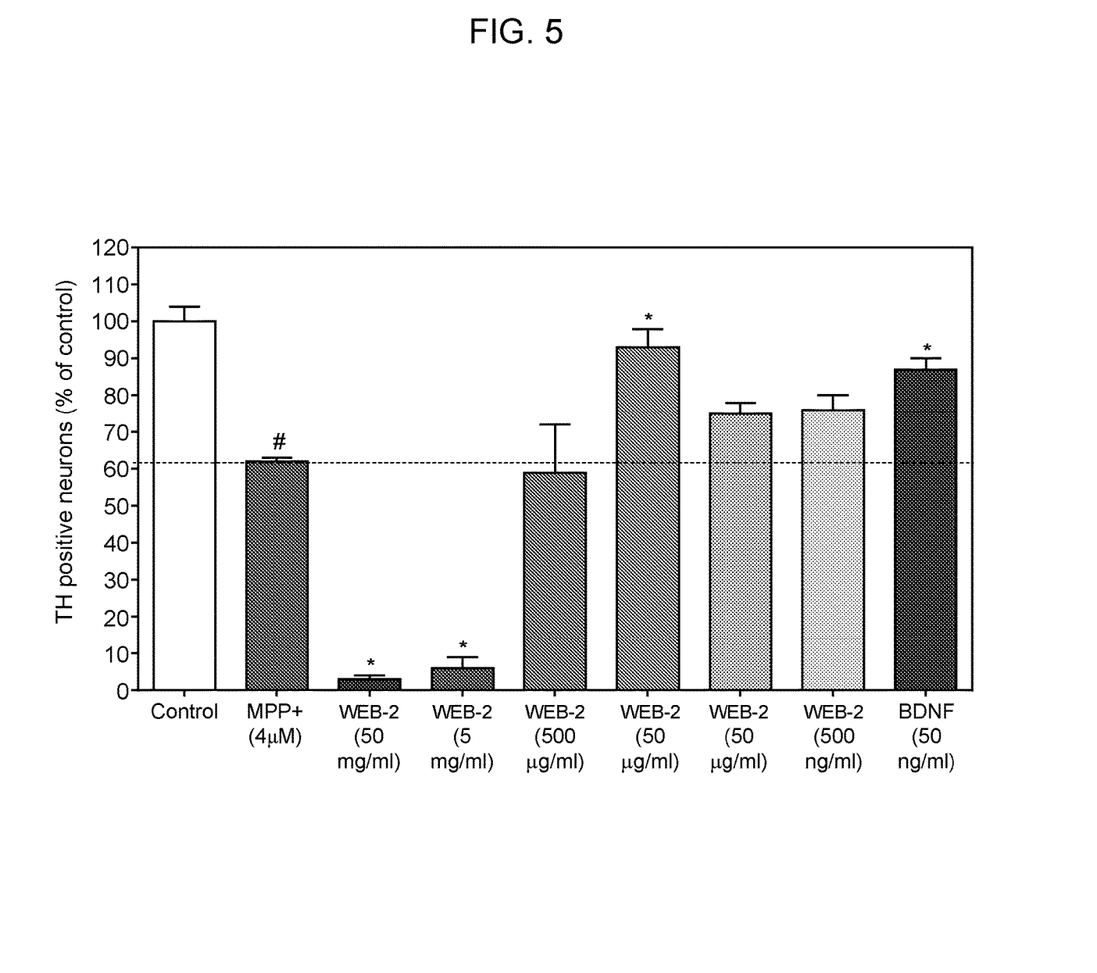
FIG. 5: Effect of MPP$^+$ (4 µM, 48 hours) in presence or absence of Plant extract WEB-2 or BDNF (50 ng/mL) on TH positive dopaminergic neuron survival of primary mesencephalic culture. Data were expressed as percentage of control as mean±SEM (100%=no MPP$^+$). # p<0.05 Control vs MPP$^+$ group; *p<0.05 vs MPP$^+$ (one way ANOVA followed by Dunnett's test).

The results show that MPP$^+$ (4 µM-48 h) induced a significant cell death (>35%). In presence of WEB-2 composition (50 µg/mL), a massive significant protective effect was observed (93% of survival) (FIG. 5).

BNDF (50 ng/mL) used as reference compound, was able to significantly protect cells from MPP$^+$ induced injuries but, interestingly, this neuroprotective effect was higher than the one observed with BDNF treatment. Additionally, this effect was still observed at the lowest doses (5 µg/mL and 500 ng/mL).

At the 2 highest concentrations (50 and 5 mg/mL), the WEB-2 composition was toxic. Therefore, the range of active concentrations seemed around the 500 µg/mL dose.

e) Conclusion

MPP$^+$ (4 µM-48 h) applied on primary mesencephalic culture induced a significant TH positive neuron (dopaminergic neurons) death.

WEB-2 extract, tested at 50 µg/mL showed an important and significantly neuro-protective effect on MPP$^+$ induced injuries, more important than the effect observed with BDNF at 50 ng/mL.

The range of the most active doses of WEB-2 extract seemed starting at 500 µg/mL with a maximal effect at 50 µg/mL.

Example 12: Tests of Different Plant Extracts

The aim of this study was to test 2 different extracts (WEB-1 and BE-2 at different concentrations (500 ng/mL, 1, 5, 10, 50, 100, 500 µg/mL and 1 mg/mL) on TH positive neuron survival after a MPP$^+$ injury.

a) Culture of Mesencephalic Neurons

The mesencephalic neurons were cultivated as in preceding example.

On day 6 of culture, the medium was removed and fresh medium was added, without or with MPP$^+$ (Batch 092M4729V, Sigma, France) at 4 µM diluted in control medium. 6 wells per condition were assessed.

b) MPP+ Exposure

On day 6 of culture, the plant extracts (500 ng/mL, 1, 5, 10, 50, 100, 500 µg/mL and 1 mg/mL) were solved in culture medium and then pre-incubated with primary mesencephalic neurons for 1 hour before the MPP$^+$ application. MPP$^+$ solution was added to a final concentration of 4 µM diluted in control medium in presence of plant extracts.

c) Immunostaining

The cells were fixed, washed, permeabilized and non-specific sites were blocked. Then, cells were incubated with Monoclonal Anti-Tyrosine Hydroxylase and revealed with Alexa Fluor 488 goat anti-mouse IgG like in example 11.

d) Results

The immunolabeled cultures were automatically examined with ImageXpress (Molecular Devices, United Kingdom) equipped with a LED at ×10 magnification. For each condition (6 culture wells), 20 automatically fields per well (representing ~80% of the total surface of the well) were analyzed. The total number of TH neurons was automatically analyzed using MetaXpress software (Molecular Devices).

Data were expressed in percentage of control conditions (no MPP$^+$=100%) in order to express the MPP$^+$ injury. All values were expressed as mean+/−SEM (s.e.mean) of the 6 wells with statistical analyses on the different conditions (ANOVA followed by Dunnett's test when allowed, using GraphPad Prism software).

MPP$^+$ (4 µM-48 h) induced a significant cell death (>30%).

Figure 6:
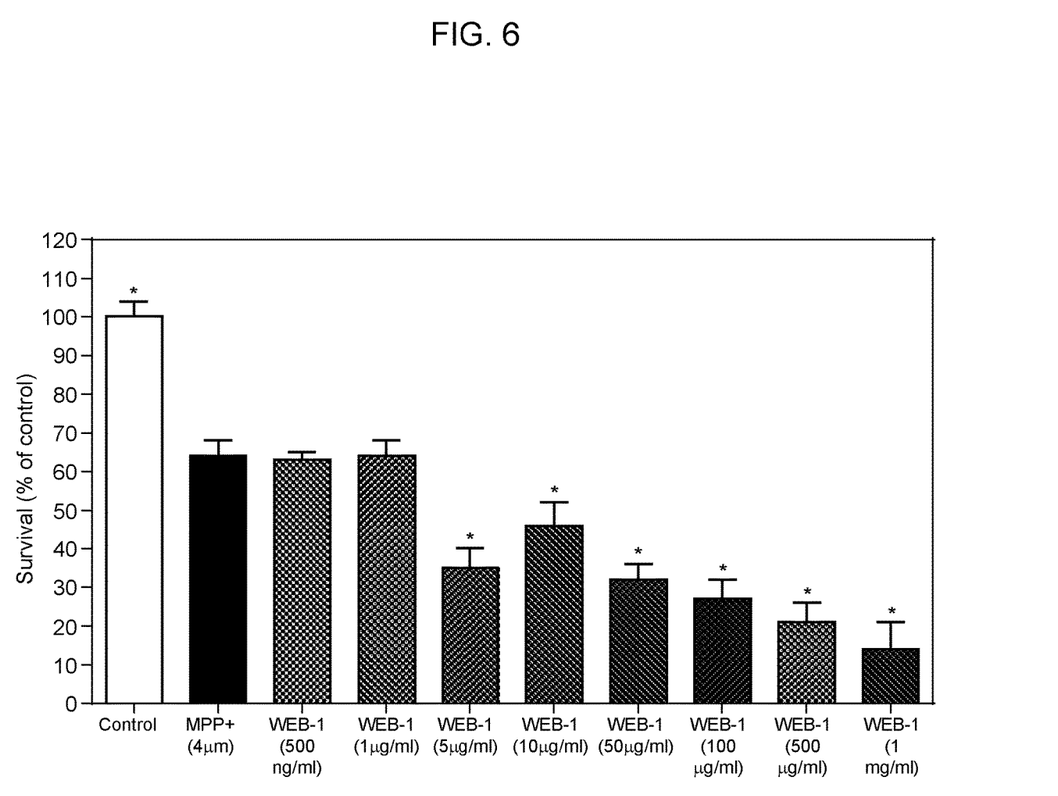
FIG. 6: Effect of MPP$^+$ (4 µM, 48 hours) in presence or absence of WEB-1 (different concentrations) on TH positive dopaminergic neuron survival of primary mesencephalic culture. Data were expressed as percentage of control as mean±SEM (100%=no MPP$^+$). *p<0.05 vs MPP$^+$ condition (one way ANOVA followed by PLSD Fisher's test).

In presence of WEB-1 (from 5 µg/mL and highest concentrations), a large and significant toxic effect was observed. Only the 2 lowest doses (500 ng/mL and 1 µg/mL) were inactive (FIG. 6).

Pre-incubation of 1 h with BE-2 induced a significant protective effect against the MPP$^+$ induced damages for the 1, 5 and 10 µg/mL doses. The lowest concentration was inactive (500 ng/mL), by contrast above 50 µg/mL BE-2 increased the toxicity of MPP$^+$.

Figure 7:
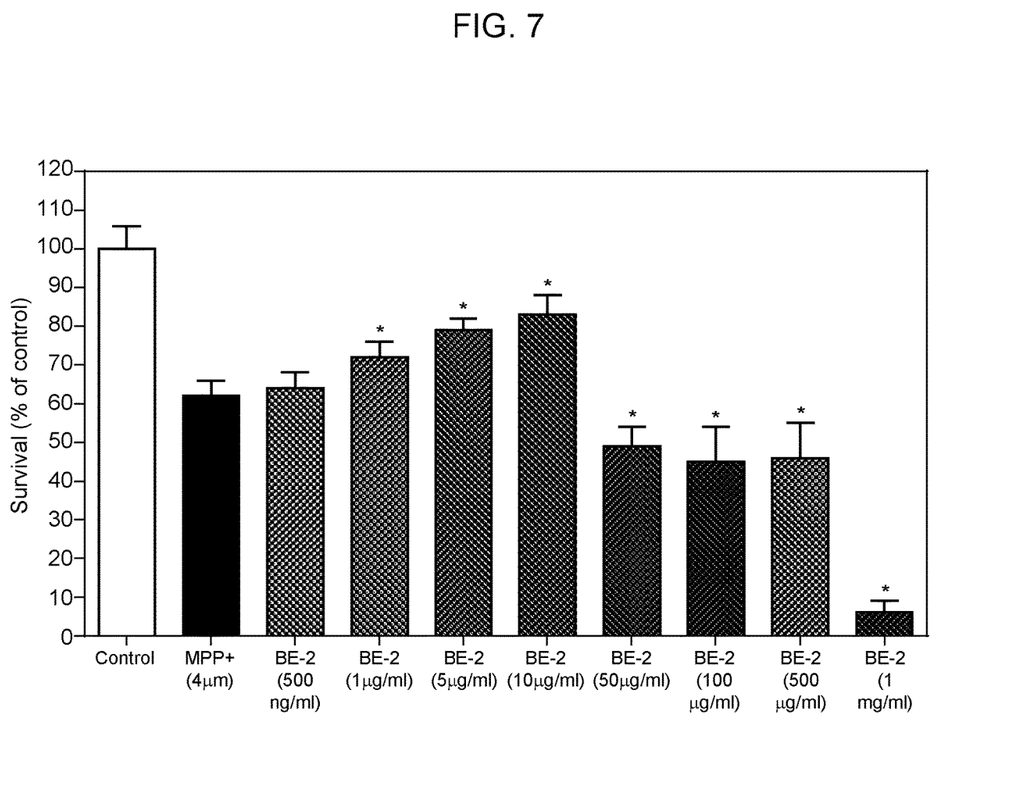
FIG. 7: Effect of MPP$^+$ (4 µM, 48 hours) in presence or absence of BE-2 (different concentrations) on TH positive dopaminergic neuron survival of primary mesencephalic culture. Data were expressed as percentage of control as mean±SEM (100%=no MPP$^+$). *p<0.05 vs MPP$^+$ condition (one way ANOVA followed by PLSD Fisher's test).

The neuroprotective effect of BE-2 increased with the dose and became toxic since 50 µg/mL concentration (FIG. 7).

c) Conclusion

MPP$^+$ (4 µM-48 h) applied on primary mesencephalic culture induced a significant TH positive neuron (dopaminergic neurons) death.

WEB-1 was inactive at lowest concentrations or toxic for TH dopaminergic neurons.

BE-2 was protective against the injuries induced by MPP+ with a range of activity between 1 up to 10 μg/mL.

Example 13: Neuroprotective Effect Following Exposure to Rotenone

This study investigated the neuroprotective effect of the plant extract of the invention WEB-2 (pretreatment and reversion application) on rat primary mesencephalic cultures following exposure to rotenone (10 nM, 24 h), an in vitro PD model.

c) Culture of Mesencephalic Neurons

The mesencephalic neurons were cultivated as in preceding example.

On day 6 of culture, the medium was removed and fresh medium was added, without or with rotenone (Batch: 021M2227V, Sigma) at 10 nM diluted in control medium, 6 wells per condition were assessed.

d) Rotenone Exposure

On day 6 of culture, the WEB-2 plant extract (500 ng/mL, 1, 5, 10, 50, 100, 500 μg/mL and 1 mg/mL) was solved in culture medium and then pre-incubated with primary mesencephalic neurons for 1 hour before or 4, 8 or 12 h after the rotenone application. Rotenone solution was added to a final concentration of 10 nM diluted in control medium in presence of WEB-2 and tested in 96 well plates (6 wells per conditions).

e) Immunostaining

The cells were fixed, washed, permeabilized and non-specific sites were blocked. Then, cells were incubated with Monoclonal Anti-Tyrosine Hydroxylase and revealed with Alexa Fluor 488 goat anti-mouse IgG like in example 10.

Tyrosine hydroxylase is involved in the conversion of phenylalanine to dopamine. As the rate-limiting enzyme in the synthesis of catecholamines, tyrosine hydroxylase has a key role in the physiology of adrenergic neurons. Tyrosine hydroxylase is regularly used as a marker for dopaminergic neurons, which is particularly relevant for research into Parkinson's disease.

f) Results

The immunolabeled cultures were automatically examined with ImageXpress (Molecular Devices) equipped with a LED at ×10 magnification. For each condition (6 culture wells), 20 automatically fields per well (representing ~80% of the total surface of the well) were analyzed. The total number of TH neurons was automatically analyzed using MetaXpress software (Molecular Devices).

Data were expressed in percentage of control conditions (no intoxication, no rotenone=100%) in order to express the rotenone injury. All values were expressed as mean+/−SEM (s.e.mean) of the 6 wells. Neuro-Sys performed graphs and statistical analyses on the different conditions (ANOVA followed by Dunnett's test when allowed, using GraphPad Prism software).

Figure 8:
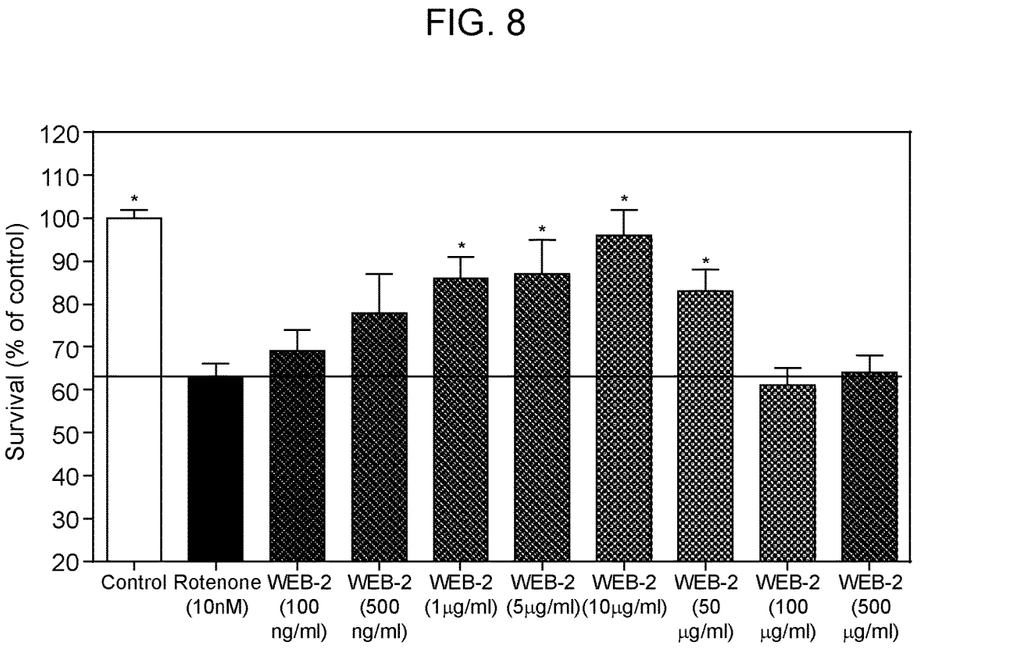
FIG. 8: Effect of rotenone (10 nM, 24 hours) in presence or absence of WEB-2 at 1 hour before rotenone (different concentrations) on TH positive dopaminergic neuron survival of primary mesencephalic culture. Data were expressed as percentage of control as mean±SEM (100%=no rotenone). *p<0.05 vs rotenone (one way ANOVA followed by PLSD Fisher's test).

Rotenone (10 nM, 24 hours) induced a significant cell death (~40%). With WEB-2 pre-incubated 1 h before rotenone application, a full significant protective effect was observed (~100% of survival) for the dose of 10 μg/mL. Similarly significant protective effect was observed for 1, 5 and 50 μg/mL (FIG. 8).

The 2 highest doses (100 μg/mL and 500 ng/mL) did not show any effect on TH positive neurons.

Figure 9:
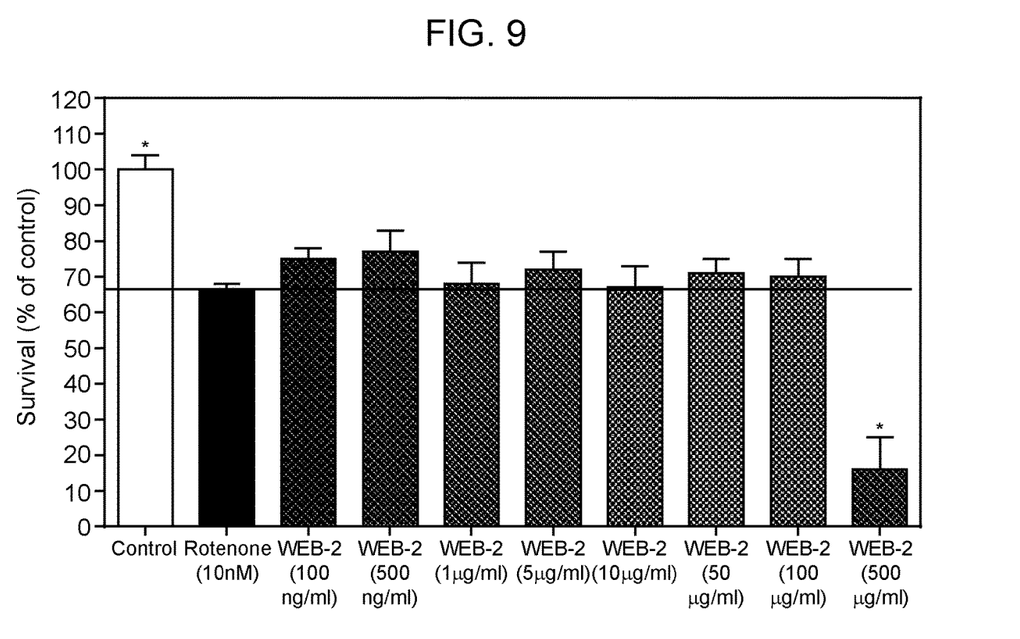
FIG. 9: Effect of rotenone (10 nM, 24 hours) in presence or absence of WEB-2 at 4 hours after rotenone (different concentrations) on TH positive dopaminergic neuron survival of primary mesencephalic culture. Data were expressed as percentage of control as mean±SEM (100%=no rotenone). *p<0.05 vs rotenone (one way ANOVA followed by PLSD Fisher's test).

WEB-2 added 4 h after the application of rotenone, did not show any effect on TH neuron survival. The highest dose (500 μg/mL) of WEB-2 was toxic (FIG. 9).

Figure 10:
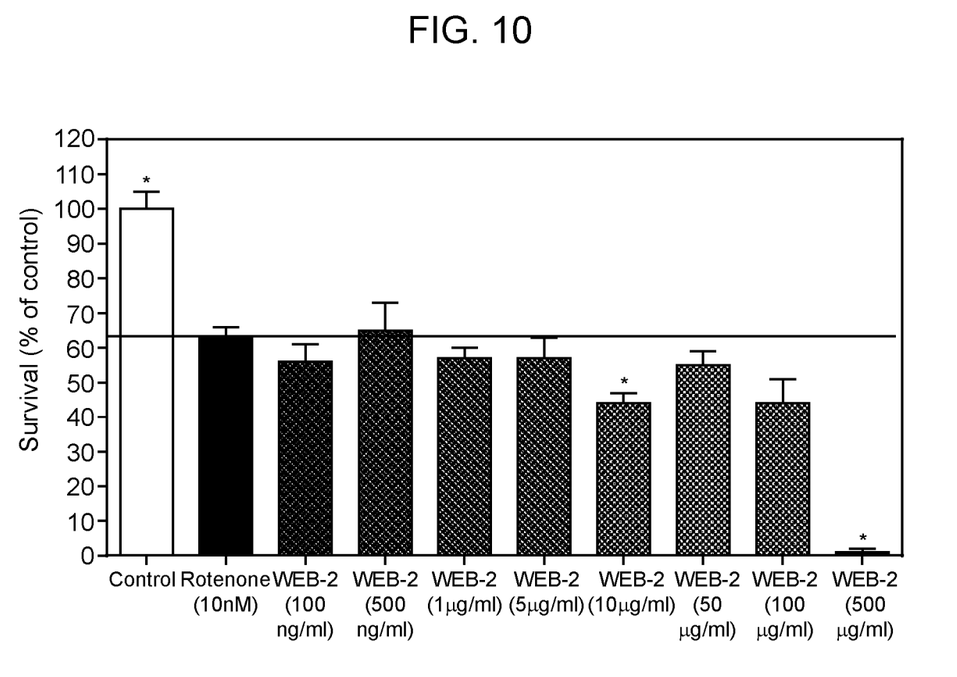
FIG. 10: Effect of rotenone (10 nM, 24 hours) in presence or absence of WEB-2 at 8 hours after rotenone (different concentrations) on TH positive dopaminergic neuron survival of primary mesencephalic culture. Data were expressed as percentage of control as mean±SEM (100%=no rotenone). *p<0.05 vs rotenone (one way ANOVA followed by PLSD Fisher's test).
Figure 11:
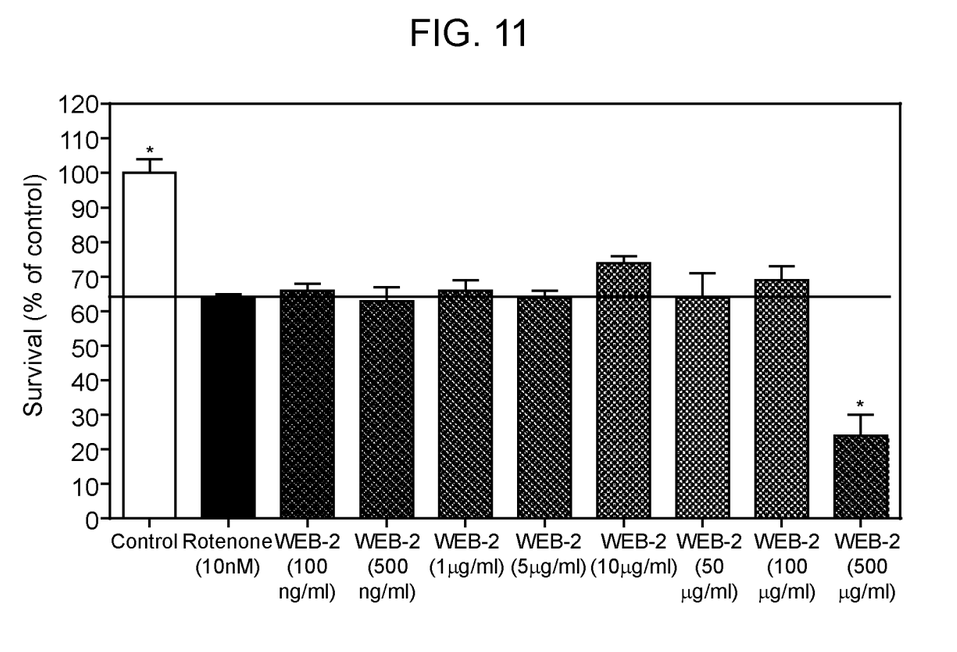
FIG. 11: Effect of rotenone (10 nM, 24 hours) in presence or absence of WEB-2 at 12 hours after rotenone (different concentrations) on TH positive dopaminergic neuron survival of primary mesencephalic culture. Data were expressed as percentage of control as mean±SEM (100%=no rotenone). *p<0.05 vs rotenone (one way ANOVA followed by PLSD Fisher's test).

Similarly, WEB-2 added 8 h after the toxin application did not show any effect on survival (FIG. 10). Highest dose was toxic. WEB-2 added 12 h after rotenone application shows toxicity at the highest dose (500 μg/mL) (FIG. 11).

All the other doses were inactive.

g) Conclusion

Rotenone (10 nM-24 h) applied on primary mesencephalic culture induced a significant TH positive neuron (dopaminergic neurons) death.

WEB-2 was able to significantly protect TH positive neurons from Rotenone injuries when applied in a protective treatment (1 h before the toxin application), by contrast added after the rotenone application no effect was observed.

WEB-2 was able to protect neurons from the rotenone toxicity but was unable to reverse or to stop the damage induced by the toxin.

The invention claimed is:

1. Composition containing a *Withania somnifera* extract fermented by incubation of the *Withania somnifera* extract with a filamentous fungus from the genus *Beauveria* in a suitable environment for a use of the composition to treat or prevent α-synucleinopathies in a mammal.

2. Composition according to claim 1, further containing at least one extract from the following plants: *Emblica officinalis, Bacopa monnieri, Punica granatum, Curcuma longa, Piper longum,* or *Calendula officinalis*.

3. Composition according to claim 1, further containing an extract of *Emblica officinalis* and an extract of *Bacopa monnieri*.

4. Composition according to claim 1, comprising a quantity by weight of *Withania somnifera* of between 5 and 100 g/L of *Withania somnifera*.

5. Composition according to claim 1, comprising a quantity by weight of *Withania somnifera* at a concentration of 20 g/L, of *Emblica officinalis* at a concentration of 15 g/L, and of *Bacopa monnieri* at a concentration of 15 g/L.

6. Composition according to claim 1, for use to treat or prevent Parkinson's disease, Lewy body dementia, multiple system atrophy, Lewy body dysphagia, neuroaxonal dystrophies, and neurodegeneration with brain iron accumulation type I.

7. A method of preventing, treating, or delaying the progression of an α-synucleinopathy in a subject, comprising administering to a subject a therapeutic amount of a composition containing a *Withania somnifera* extract fermented by incubation of the *Withania somnifera* extract with a filamentous fungus from the genus *Beauveria* in a suitable environment, such that said α-synucleinopathy in the subject is treated or prevented.

8. The method of claim 7, wherein said disease is selected from the group consisting of Parkinson's disease, Lewy body dementia, multiple system atrophy, Lewy body dysphagia, neurodegeneration with brain iron accumulation type I, and pure autonomic failure.

9. The method of claim 7, wherein said subject is a human.

10. The method of claim 7, wherein the method prevents, treats, or delays the progression of one or more impairments associated with Parkinson's disease in a patient with Parkinson's disease.

11. The method of claim 7, wherein the method prevents, treats, or delays the progression of dementia associated with Parkinson's disease in the subject.

12. The method of claim 7, wherein the composition is administered orally or intravenously.

13. The method of claim 7, wherein the composition is administered in a pharmaceutically acceptable vehicle.

* * * * *